United States Patent
Saunders (10) Patent No.: US 7,313,224 B1
(45) Date of Patent: Dec. 25, 2007

(54) WIRELESS INTEGRATED AUTOMATIC EXPOSURE CONTROL MODULE

(75) Inventor: Rowland F. Saunders, Hartland, WI (US)

(73) Assignee: General Electric Co., Schenectady, NY (US)

( * ) Notice: Subject to any disclaimer, the term of this patent is extended or adjusted under 35 U.S.C. 154(b) by 0 days.

(21) Appl. No.: 11/426,009

(22) Filed: Jun. 22, 2006

(51) Int. Cl.
*H05G 1/42* (2006.01)

(52) U.S. Cl. ........................ 378/108; 378/109

(58) Field of Classification Search .............. 378/108, 378/97, 109–112

See application file for complete search history.

(56) References Cited

U.S. PATENT DOCUMENTS

| | | | | |
|---|---|---|---|---|
| 6,151,383 | A * | 11/2000 | Xue et al. | 378/108 |
| 7,177,392 | B2 * | 2/2007 | Shefer et al. | 378/108 |
| 2001/0048734 | A1 * | 12/2001 | Uppaluri et al. | 378/207 |

* cited by examiner

*Primary Examiner*—Hoon Song
(74) *Attorney, Agent, or Firm*—Peter Vogel, Esq.; Michael G. Smith, Esq.

(57) ABSTRACT

Systems and methods for providing independent exposure detection, X-ray spectrum and timing compensation, and providing an exposure termination signal to an X-ray system. The system incorporates an interface for receiving exposure characteristic data such as kVp, spectral filter, and focal spot. The system through a programmed controller determines one or more control parameters based on the received exposure characteristic data and generates a control signal for controlling an X-ray source.

20 Claims, 6 Drawing Sheets

WIRELESS INTEGRATED AUTOMATIC EXPOSURE CONTROL MODULE

FIELD OF THE INVENTION

The field of the invention is X-ray imaging systems, and particularly, automatic exposure control and exposure optimization for X-ray systems through a wireless integrated automatic exposure control module.

BACKGROUND OF THE INVENTION

Automatic exposure control (AEC) is used in X-ray imaging equipment to control the exposure per image. The goal is to maintain image quality while minimizing patient exposure. The AEC develops a signal proportional to the X-ray flux into the image receptor. This signal is used to regulate the total exposure for each image either by terminating the exposure or by adjusting the X-ray flux rate. In this usage, the X-ray technique (kVp, spectral filter, focal spot, etc) is prescribed by the operator. Often these are preset and selected based on patient size and anatomy to be imaged. Thus, the role of the AEC is to regulate the correct total exposure.

Generally, an incident radiation dose must be adjusted for each object or every imaging. Conventionally, an AEC control sensor is arranged independently of the imaging radiation detector. Pluralities of thin AEC sensors that attenuate radiation by about 5% are separately arranged in front of the imaging radiation detector. Incidence of radiation is stopped based on the outputs from the AEC sensors, thereby obtaining an appropriate radiation dose for imaging. As an AEC sensor, a sensor which directly extracts radiation as charges by using an ion chamber, or a sensor which converts radiation into visible light through a phosphor, extracts the visible light through an optical fiber, and causes a photomultiplier to convert the visible light into charges is used. This analog output is routed over a long cable to the X-ray control where the signal is compared to a reference voltage representing the required exposure. The typical interface to the ion chamber includes an ion chamber selection, an exposure start signal, and a power supply as inputs and an analog integrated brightness as the output.

The spectral sensitivity of these devices is neither constant over the required kVp range nor can it exactly match the characteristics of the recording medium. The recording medium may be a film screen cassette, CR cassette or a flat panel detector.

The temporal response of the ion chamber design does not account for limitations in the exposure control system. Very long exposures for film require system level AEC compensation to increase the required exposure to compensate for reciprocity loss, also called the Swartzchild effect. Very short exposures require an anticipation function to reduce the required exposure to compensate for the delays in the ion chamber itself as well as rise and fall time limitations in the X-ray generator.

The spectral and temporal response characteristics require calibration at a system level to provide acceptable system performance. In some systems the required compensations are partially incorporated in the design of the system level AEC. In some cases the AEC calibration is one of the longer tasks in the system calibration process.

Yet another drawback with conventional automatic exposure control is when ion chamber characteristics are embedded in the system level AEC design, then changing ion chamber designs or suppliers requires a new software release to incorporate any differences in performance.

For the reasons stated above, and for other reasons stated below which will become apparent to those skilled in the art upon reading and understanding the present specification, there is a need in the art for an integrated automatic exposure control (AEC) subsystem. There is also a need for improved signal to noise, accuracy and small signal sensitivity in an automatic exposure control (AEC).

BRIEF DESCRIPTION OF THE INVENTION

The above-mentioned shortcomings, disadvantages and problems are addressed herein, which will be understood by reading and studying the following specification.

In one embodiment, an exposure control device providing independent exposure detection, X-ray spectrum and timing compensation, and providing an exposure termination signal to the X-ray system. The exposure control device incorporates an interface for receiving exposure characteristic data such as kVp, spectral filter, focal spot; a controller for determining one or more control parameters based on the received exposure characteristic data; and, a device for generating a control signal upon the occurrence of one or more control parameters.

In yet another embodiment, integrated automatic exposure control takes the ion chamber design from a simple sensor to what is often called a smart sub-subsystem. The knowledge of required spectral, timing and other relevant acquisition related information is shifted from the system design to the subsystem. The exposure start either can be an explicit command or determined through analysis of the integrated signal. System level performance limitations can be incorporated into this subsystem to improve signal-to-noise-ratios.

In another embodiment, an exposure control device providing independent exposure detection, X-ray spectrum and timing compensation, and providing an exposure termination signal to the X-ray system. The exposure control device incorporates an interface for receiving exposure characteristic data. This exposure characteristic data could include the area selection, kVp, grid information, and the "speed" to be used. Speed is related to the required exposure in mR at some reference point. A controller for determining one or more control parameters based on the received exposure characteristic data, and a device for generating a control signal upon the occurrence of one or more control parameters. The interface can be totally digital, either electrical or optical. The SNR (signal to noise) of the AEC design is improved by converting the analog signal to digital as close as possible to the signal source. This supports the interest in minimizing dose for some radiographic exam types like for pediatric patients.

In still another embodiment, a calibration module is used to accomplish calibration at the subsystem level. Only a functional check is required at a system level. The calibration is done in a more controlled environment. An alternate set of calibrations can be downloaded to the subsystem to address changes in system design or for experimental investigations. Calibrations for numerous system types could be included with the sub-system. Additional calibration updates could be handled in the same manner typically used for personal computer driver updates.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into sections for the purpose of describing certain aspects of the invention. In one section, a system level overview and/or particular implementations are described. In another section, methods of embodiments are described. In yet another section, the hardware and the operating environment in conjunction with which embodiments may be practiced are described. The final section is a conclusion of the detailed description as provided in the preceding sections.

System Level Overview

Figure 1:
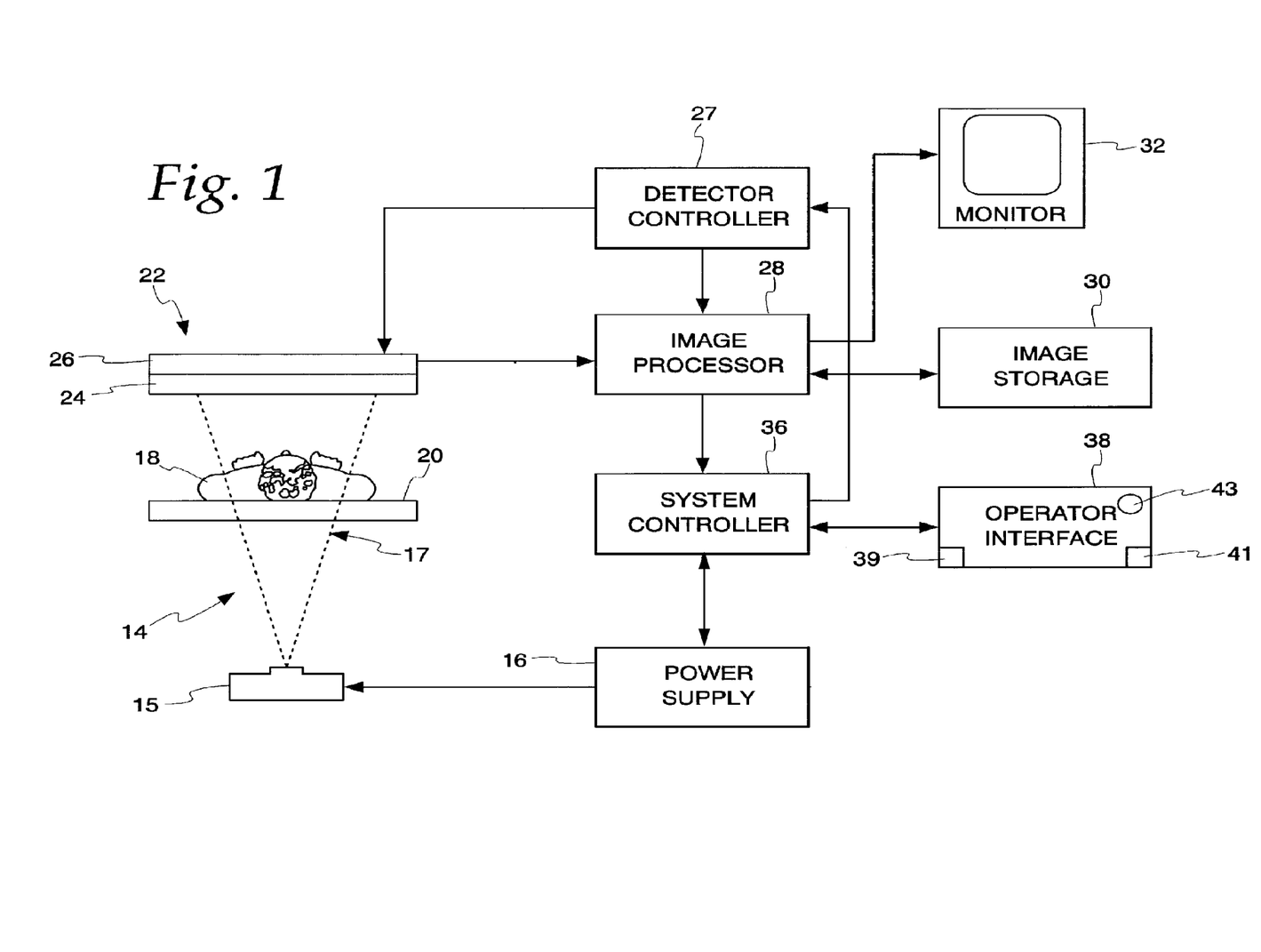
FIG. 1 is a diagram illustrating a system-level overview of an embodiment.

FIG. 1 is a block diagram that provides a system level overview. Embodiments are described as operating in a multi-processing, multi-threaded operating environment on a computer, such as computer 502 in FIG. 5.

FIG. 1, an X-ray system 14 includes an X-ray tube 15 or X-ray source 15 which, when excited by a power supply 16, emits an X-ray beam 17. As illustrated, the X-ray beam is directed toward a patient 18 lying on an X-ray transmitting table 20. The portion of the beam, which is transmitted through the table and the patient, impinges upon an X-ray detector assembly 22. The X-ray detector assembly 22 comprises a scintillator 24 that converts the X-ray photons to lower energy photons in the visible spectrum. Contiguous with the scintillator 24 is an image photo detector array 26, which converts the light photons into an electrical signal. A detector controller 27 contains electronics for operating the detector array 26 to acquire an image and to read out the signal from each photo detector element.

The output signal from the image photo detector array 26 is coupled to an image processor 28 that includes circuitry for collecting, processing and enhancing the X-ray image signal. The processed image is displayed on a video monitor 32 and may be stored in an image storage device 30. A system and image detector controller 36, which receives commands from the user via an operator interface panel 38, including a prep switch 39 and an exposure switch 41, governs the overall operation of the X-ray apparatus 14. A light 43 is illuminated during various modes of operation as will be described later.

Figure 3:
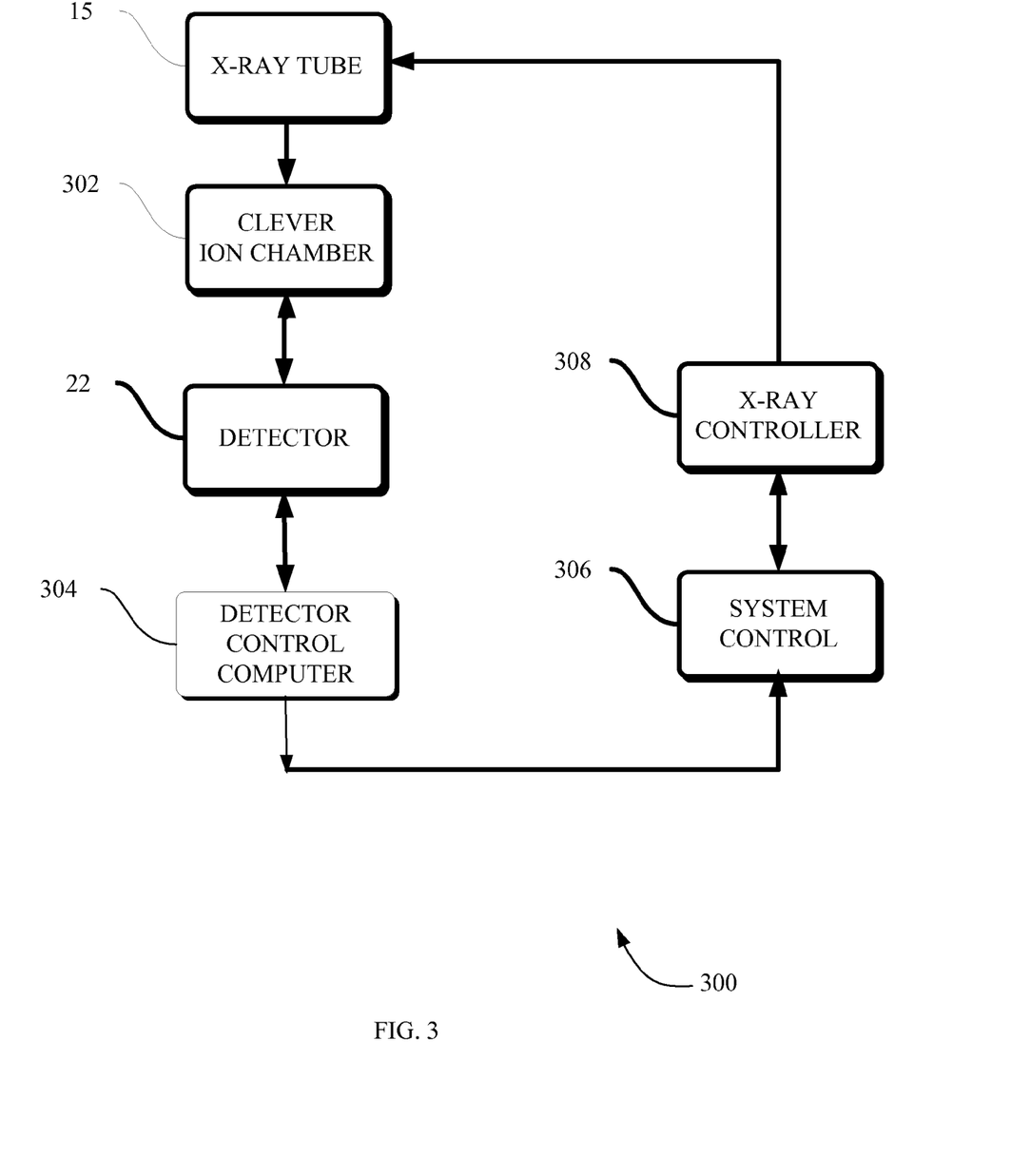
FIG. 3 is a block diagram of the clever ion chamber environment in which different embodiments can be practiced.
Figure 4:
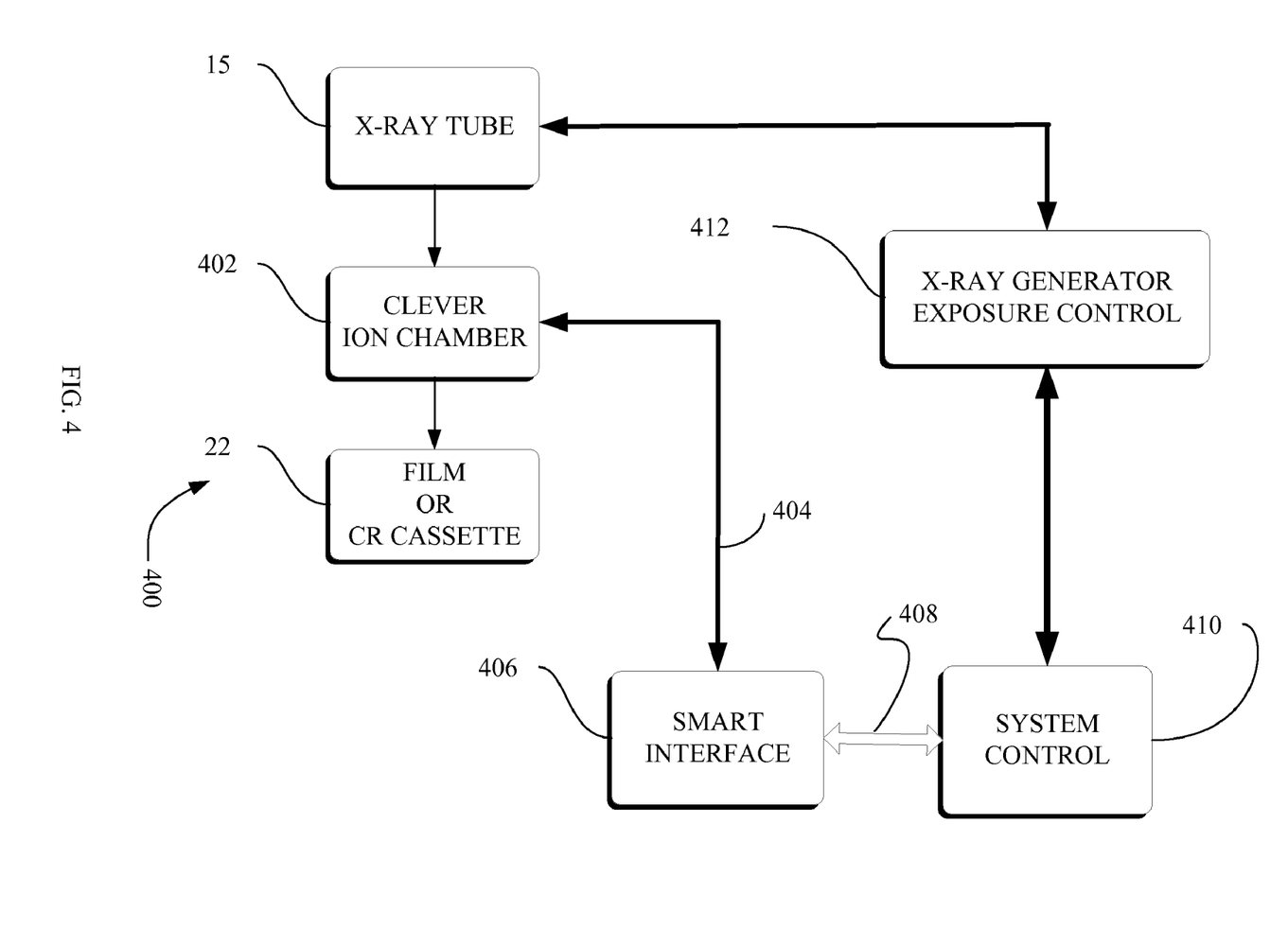
FIG. 4 is a block diagram of the clever ion chamber and the smart interface in which different embodiments can be practiced.

The image photo detector array 26 consists of amorphous silicon devices on a glass substrate. A portion of the light from the scintillator 24 is transmitted through these silicon devices and through the spaces between them. In addition, some of the X-rays are transmitted through both the scintillator 24 and the image photo detector array 26. The output signal from array 26 also is coupled to an exposure control circuit (not shown) that is described in FIGS. 2-4.

Generally the imaging system utilizes a Preshot image from digital detector 26. The Preshot image is obtained from a small dose of X-rays occurring before the X-ray exposure that results in an image of a patient. The number, location and size of the regions of interest (ROIs) on the Preshot image, are used for exposure control, and are defined based on a prescribed Anatomy/View or are automatically calculated from the image data created in detector 26. A typical anatomy view is a chest view. Thus, the AEC "field of view", can be adjusted for different imaging procedures by selectively combining the signal from one or more ROIs of desired shape and size.

Different image based algorithms can be used to derive the appropriate ROIs. The simplest approach is to create ROIs having the same size and shape as the ion chamber cells. In this case, the mean X-ray signals in the selected ion chambers are calculated. The X-ray detector is calibrated such that image gray values can be converted to exposure level through a conversion factor transfer function.

$$\text{Exposure(mR)} = F1(\text{gray\_level})$$

It is safe to assume that this function is linear and the slope and intercept depend upon the X-ray energy spectrum. To calculate the mAs required of the full-dose shot the preshot mAs is scaled by the measured mean gray value in the preshot image and the desired exposure level in converted gray values: Required mAs=preshot_mAs*F1(desired_exposure)/preshot_ROI_gray_level For example, a preshot with mAs (milli-amp-seconds) of 0.1 is used with a given kvp, focal spot size, mA, etc, and the desired detected exposure level is 3.4 micro R. The system has been calibrated such that the conversion factor is known to be 300 counts/micro_R. The mean value has been calculated in the ROI representing the location of the ion chambers to be 50 counts. Thus, using Required mAs relationship above:

Required $mAs = 0.1*(300*3.4)/50 = 2.04$

The automatic exposure controller now commands the system to operate at the required_mAs.

After Prepare switch 39 is pressed, the system defines the Preshot parameters based on the following parameters prescribed by a user of the system: Anatomy/View, Customer Dose selection and Patient size. Patient size generally is limited to small, medium or large. The user enters the parameters from operator interface 38. The Preshot parameters include the X-ray exposure technique, the detector timing, and the synchronization between these two. The X-ray exposure technique includes KV, ma, Mas and many other parameters known to X-ray technicians. The detector timing includes offset timing and readout time. Through interface 38, a user enters all of the Preshot parameters.

After Expose switch 41 is pressed, the system performs the following actions generating an Offset image; Acquiring a Preshot image; Calculation of optimal X-ray dosage, for example, by adjusting exposure time; and Generating an exposure or Final image based on calculated optimal X-ray dosage.

The system calculates exposure time based on a required signal to noise ratio (SNR) by performing the following steps: Storing the required $SNR_{req}$ value for a particular Anatomy/View; Measuring $SNR_{meas}$ on Preshot image inside predefined (or calculated) ROIs; Calculating the ratio $SNR_{req}/SNR_{meas} = K$, $SNR \propto T$; and Calculating $T_{exp} = K^2 \times T_{preshot}$.

The SNR is the signal to noise ratio, K is the predefined ratio of final exposure to the preshot exposure, and T is the exposure time of the X-ray pulse.

The Preshot exposure (image) may be acquired in reduced matrix size (e.g. 128.times.128 as opposed 2,000.times.2,000 pixels) for the same field of view (FOV) in order to minimize the extra time. For example, the preshot X-ray technique is defined as the predetermined kVp with exposure time to "fit" within the preshot expose window (<10 msec (milliseconds)) and the mA to deliver the requested exposure (5-10% of a "normal" dose used to generate a diagnostic image of a patient). In other words, the X-ray dosage during the normal exposure is 10 to 50 times greater than the X-ray dosage during the pre-exposure preshot step. The predetermined kVp typically may vary, for example, from 40 to 150 kVp. The Preshot exposure window varies as needed up to about 10 milliseconds depending on the selected anatomy of the patient and the selected view. The Preshot function adds about 20 ms to total acquisition time.

In one simple embodiment, the Preshot analysis simply calculates image statistics on rectangular regions of interest that mimic the current ion chamber positions (although no ion chamber is used in the preferred embodiment). The final image technique may be calculated to achieve a particular mean target signal level (or target dose) or to attain a particular signal to noise ratio. More sophisticated algorithms may analyze the image to locate particular anatomical features. For example, the image may be segmented using thresholding or analysis to identify the regions of interest to perform statistical analysis. A preferred segmentation method utilizes a mixture of spatial and statistical algorithms. The collimator and raw radiation areas are removed using morphological operations, such as dilation and erosion operations with pre-selected kernel sizes and/or. Next, the anatomical contents are delineated using a gradient filter that identifies boundaries. With a gradient image, the edges or object boundaries are assigned a high absolute value, and flat areas are assigned a value of 0. An edge-strength threshold is calculated based upon the X-ray system patient input dose and the expected (heuristic) values based upon the patient anatomy. For example, an image threshold may be calculated based on an estimate of noise in the image (such as by using standard deviation in a flat region) divided by the patient input dose times a scalar that depends upon the anatomy. The output is a set of non-rectangular regions of interest, presumably from different anatomical features. The outputs of the segmentation algorithm are multiple regions of interest (ROIs) for different anatomical areas. Certain ROIs are selected based on a set of predefined rules using the size, shape, and gray level statistics such as min, mean, max, and standard deviation. In segmentation, the system focuses on the area surrounding the anatomy of interest, and the rest of the image may be ignored. As an example, the throat/larynx and spine form a patient segment of interest for a neck image acquisition. The system focuses on the segment of the medical diagnostic image comprising the throat, larynx, and spine in analyzing a neck image. As an example, the lungs and diaphragm form a segment of interest in a patient image for a chest image acquisition. The segment of the medical diagnostic image comprising the lungs and diaphragm is identified and the segment of interest for a chest image acquisition. The anatomy of interest is analyzed to identify at least one of a set of anatomy image characteristics, such as patient thickness.

The characteristics may be used to characterize the anatomical segments of interest. The anatomical segments of interest may be characterized in terms of patient parameters, such as the attenuation of the segments. Patient parameters may also include the brightest and darkest regions of the anatomy of interest. The analysis may also include correlating current data with a normalized patient and/or using a mathematical model of the anatomy of interest to characterize parameters.

The optimal exposure for the final image may be at the same Preshot X-ray spectrum (kVp and spectral filter), but at a calculated mAs (mA and exposure time calculation chosen to minimize patient motion and maximize tube life). Alternatively, the Preshot analysis may change the X-ray spectrum based on predefined technique charts or calculated based on estimated patient thickness and anatomy/view. These image acquisition parameters or settings are used to adjust the X-ray acquisition techniques visualization, and/or clarity of the anatomy and pathology of interest, while minimizing dose. For example, the kVp (X-ray energy, kilo-volt energy of X-ray beam) and spectral filters may be selected to optimize the bone/soft tissue separation at the segment of interest. The mAs (milliamps times seconds) and X-ray detector gain may be chosen to minimize target dose while maintaining a sufficient signal in the most dense area of the segment of interest.

Figure 2:
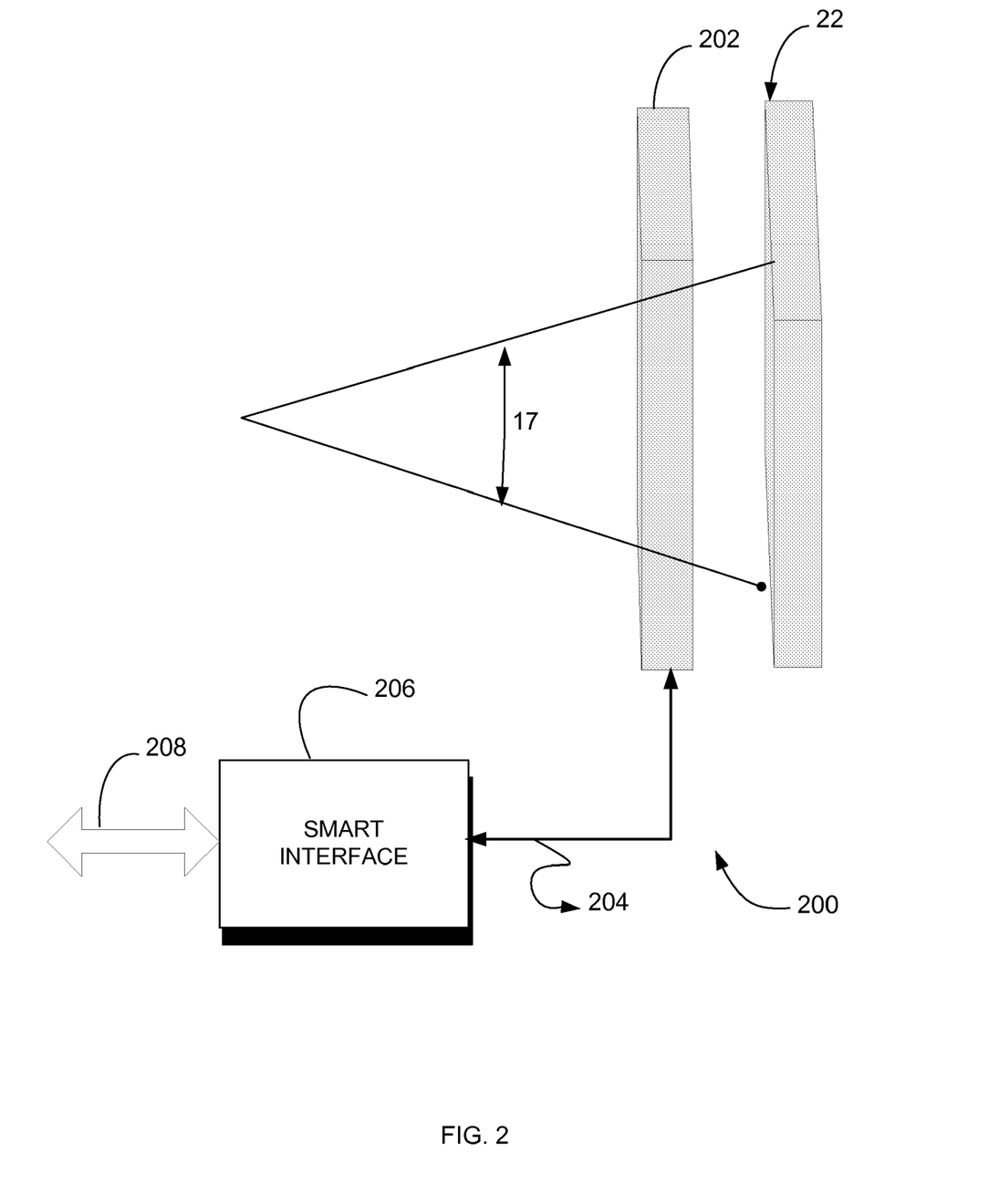
FIG. 2 is an illustration showing the apparatus position between an X-ray source and a detector according to an embodiment.

FIG. 2 is a block diagram that provides a system level overview of the smart ion chamber 200 in accordance to an embodiment. The smart ion chamber 200 consist of a smart ion chamber 202, an interface device 206 for generating and receiving signals from an external source, and a detector 22. It should be noted that the smart ion chamber 200 does not need the detector 22 for performing its primary functions. The detector 22 could be removed and what would remain is the smart ion chamber 202 that can be used to generate one or more control signals for automatic exposure control. The smart ion chamber solves the need in the art for an integrated automatic exposure control (AEC) subsystem with improved signal to noise ratio.

As noted earlier with reference to X-ray source 15, generated by an X-ray tube, passes through a patient or object on its journey to detector 22. It should be noted that detector 22 is any form of system or device for receiving an X-ray beam such as film or digital detector. For example, digital detectors typically rely on direct conversion of X-rays to charge carriers or alternatively indirect conversion in which X-rays are converted to light that is then converted to charge carriers. Operationally direct and indirect conversion based digital X-ray detectors use charge storage matrices to retain imaging information that is then electronically addressed before the next exposure. In real-time imaging is accomplished by repeatedly reading the integrated radiation values of the storage matrix (detector) to provide a sufficiently high number of frames per second. For medical diagnosis, it is desirable to use the minimum X-ray exposure dose that will provide an image having acceptable contrast and brightness. An automatic exposure control device is used to sense radiation passing there through and provide a signal which terminates the X-ray exposure when a predetermined dose value, yielding a desired radiation density level, has been reached. Alternatively, the actual X-ray exposure dose for a specific X-ray examination may be selected using predetermined imaging exposure parameters and patient characteristics loaded from periodically updated lookup tables into an X-ray system console. This table may be assembled from prior exposures by using well known statistical techniques.

Upon passing through an object the X-rays interacts with the smart ion chamber 200 which uses weakly absorbing X-ray detectors to sense the X-rays to have negligible interference on the X-ray image. The smart ion chamber 202 utilizes an X-ray sensitive ion chamber coupled with integrating electronics and a feedback control signal (AEC) to control the X-ray source 15. The smart ion chamber is an amalgamation of automatic exposure control and an ion chamber where the AEC produces signals indicative of the X-rays sensed by the AEC device. Once sufficient X-rays have passed through the patient and the chamber to produce proper film darkness on the film, or proper response of a digital detector, the X-ray generating device 15 stops generating X-rays when commanded by outside stimuli.

In order to determine if sufficient X-rays have passed through the smart ion chamber 200 such as to a video cassette recorder (cassette), the AEC output must be calibrated by determining a target AEC output for each of the sets of predetermined conditions of the imaging system 100. There are several variables that affect the set of predetermined conditions for the imaging system 100 including system level performance limitations, the patient thickness or anatomy which would affect the attenuation and spectrum of the X-rays, the X-ray generator voltage kV used to generate the X-rays, the X-ray generator 15 and X-ray tube being used, the X-ray filter, collimator, and the ion chamber. The imaging system 100 could have a plurality of sets of these conditions representing different values for each of these variables. Accordingly, for each set of predetermined conditions the system 100 must be calibrated to determine the correct or target AEC output which will result in the proper exposure of the film, elements at detector 22, or other image sensing device presently existing or to be developed in the future for sensing an image. The smart ion chamber 200 contains a calibration module to insure proper operations in view of the performance limitations noted above. During the calibration procedure, the smart ion chamber will have its various variables set to a first predetermined condition and the X-ray generating device 15 will generate X-rays for a predetermined period.

Calibration is done at the subsystem level. Only a functional check is required at an imaging system level. The calibration is done in a more controlled environment.

An alternate set of calibrations can be downloaded to the subsystem to address changes in system design or for experimental investigations. Calibrations for numerous system types could be included with the sub-system. Additional calibration updates could be handled in the same manner typically used for personal computer driver updates.

The smart ion chamber employs an interface 206 for both receiving and transmitting signals. The interface 206 to the smart ion chamber can be fully digital or hybrid digital/analog. A digital interface allows the use of wireless RF, IR, optical or other methods to be employed for receiving and transmitting data. In a fixed system the use of full digital provides the potential for improved SNR with an inexpensive wired interface. The SNR (signal to noise ratio) of the smart ion chamber is improved by converting the analog signal 204 to digital as close as possible to the signal source. This supports the interest in minimizing dose for some radiographic exam types specially pediatrics or orthopedic. Data or information such as exposure characteristic data such exposure information is transferred 208 to the subsystem prior to the exposure start. This information could include the area selection, kVp, grid information, and the "speed" to be used. Speed is related to the required exposure in mR at some reference point. The exposure start either can be an explicit command or determined through analysis of the integrated signal. The offset and drift of the design can be minimized using continual leakage compensation during standby periods. This method calculates the analog offset required to zero the integrator drift. This provides a substantial improvement in overall performance especially for long, low intensity exposures. When required the design can be battery powered, in a low current standby mode when not in use. The system would send a wakeup prior to exposure start. The unit returns to standby after a period of inactivity.

The system level overview of the operation of an embodiment has been described in this section of the detailed description. While the system 100 or 200 are not limited to any particular detector or hardware, for sake of clarity a simplified system has been described.

Methods of an Embodiment

In the previous section, a system level overview of the operation of an embodiment was described. In this section, the particular methods performed by the smart ion chamber of such an embodiment are described by reference to a series of flowcharts. Describing the methods by reference to a flowchart enables one skilled in the art to develop such programs, firmware, or hardware, including such instructions to carry out the methods on suitable processing device such as the processor of the clients executing the instructions from computer-readable media. Similarly, the methods performed by the server computer programs, firmware, or hardware are also composed of computer-executable instructions. Method 600 is performed by a client program executing on, or performed by firmware or hardware that is a part of, a computing device and is inclusive of the acts required to be taken by an aptly programmed computer.

Figure 6:
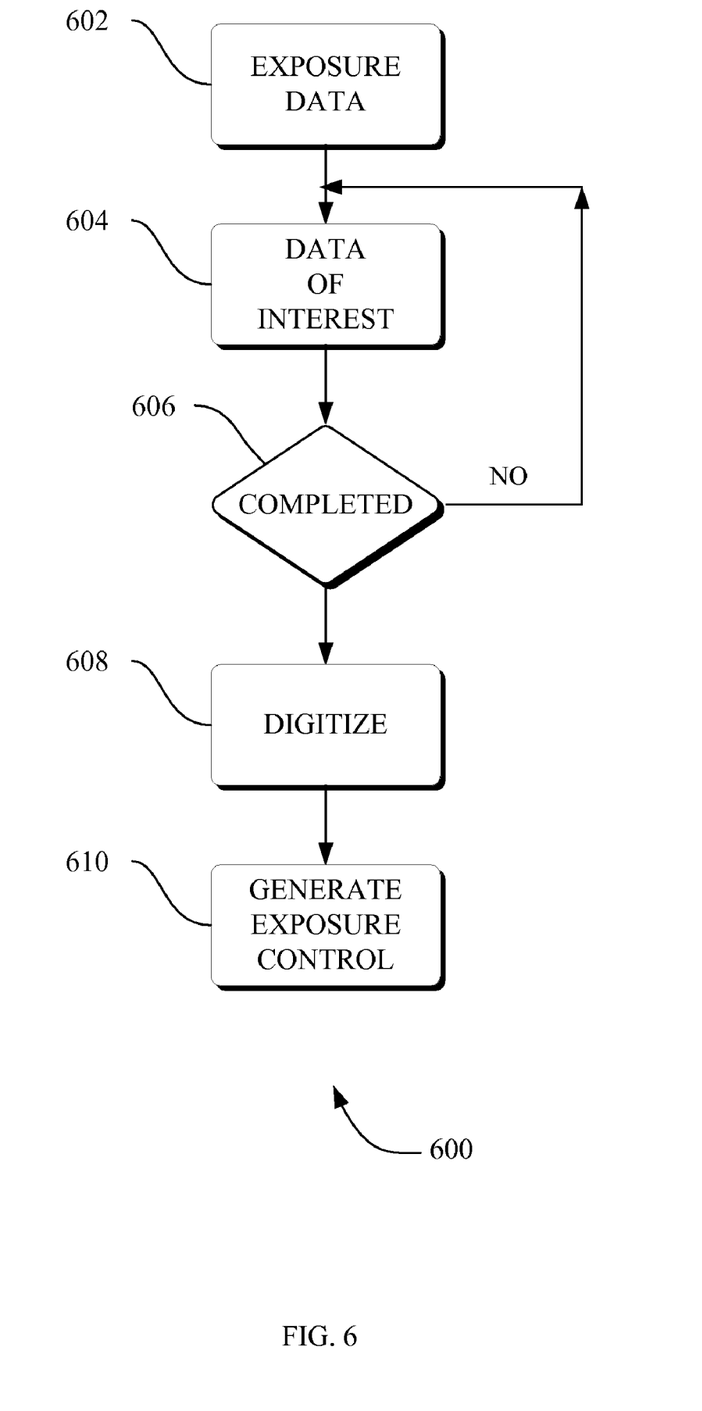
FIG. 6 is a flowchart of a method in which different embodiments can be practiced.

FIG. 6 is a flowchart of method performed by a client according to an embodiment. The term client as used herein is inclusive all devices capable of receiving an input from an external device or system, process or act in accordance to the received input, and provide to the external device or system a response in accordance to the received input. As used in this context the client is a subsystem that performs automatic exposure control functionality based on exposure characteristics received from an imaging system. The subsystem performs these functions relatively independent of the imaging system. Method 600 solves the nee in the art for an integrated automatic exposure control (AEC) subsystem having improved signal to noise and accuracy and small signal sensitivity.

Method 600 begins with action 602 receiving exposure data such as ion chamber design and performance limitation data. The exposure data could be received from the imaging system 100, from a non-volatile memory within the smart ion chamber, from volatile memory such as RAM, from an external source, or from other external sources using network such as the internet. The primary purpose of the exposure data is to convey information to the smart ion chamber so as to integrate knowledge of required spectral, timing, and other relevant acquisitions and to perform calibration and imaging system control. The exposure data could be transferred as one single download or as a series of downloads providing that it is transferred before the start of the exposure cycle. Example of information that could be transferred to the smart ion chamber before the start of the exposure cycle could include area selection, kVp, grid information, exposure start, calibration programming, and the "speed" to be used during the exposure cycle. Speed is related to the required exposure in mR at some reference point. From the calibration programming the smart ion chamber 202 can formulate a calibration procedure for the subsystem so that only a functional check is needed at the imaging system 100. In conjunction with the calibration the smart ion chamber can provide compensation during standby periods for offset and drifts due continual leakage. This method calculates the analog offset required to zero the integrator drift. This provides a substantial improvement in overall performance especially for long, low intensity exposures. Once the exposure data has been received at action 602 control passes to action 604 for further processing.

In action 604, data of interest is determined by the smart ion chamber 202. The data of interest can be exposure detection, X-ray spectrum and timing compensation, exposure termination signal, offset correction, or any other data that can be derived from the received exposure data and X-ray source detection data. Once the data of interest has been determined control passes to action 606 for further processing.

In action 606, completion is determined. The function of action 606 is to insure that all components of a data of interest have been determined by the smart ion chamber before it is transmitted to the imaging system or is used by another module. In circumstances where raw data or a selected group of data is desired decision block 606 could be removed or suppressed. Decisions block 606 forwards either to action 604 or action 608 based on the desired logic.

In action 608, the acquired data of interest from action 604 is digitized. The electrical signals are read out by a predetermined reading method and undergo analog-to-digital conversion for providing a digitized signal with improved signal-to-noise ratio. For background on analog-to-digital conversion see "The Scientist and Engineer's Guide to Digital Signal Processing, Steven W. Smith, 1998; and, "Handbook of Medical Imaging Display & Pacs", Jacob Beutel, SPIE Press (ISBN: 0819436232), 2000. Once the signal has been digitized control passes to action 610 for further processing.

In action 610, an exposure control signal is generated. The exposure control signal can be one or more exposure start signal, low current standby signal when not in use, exposure start wakeup signal, spectrum compensation, timing compensation, or exposure termination. Once the exposure signal has been generated at action 610 control passes to the appropriate device or the appropriate process module for action consistent with the functionality of the device or process module.

Figure 5:
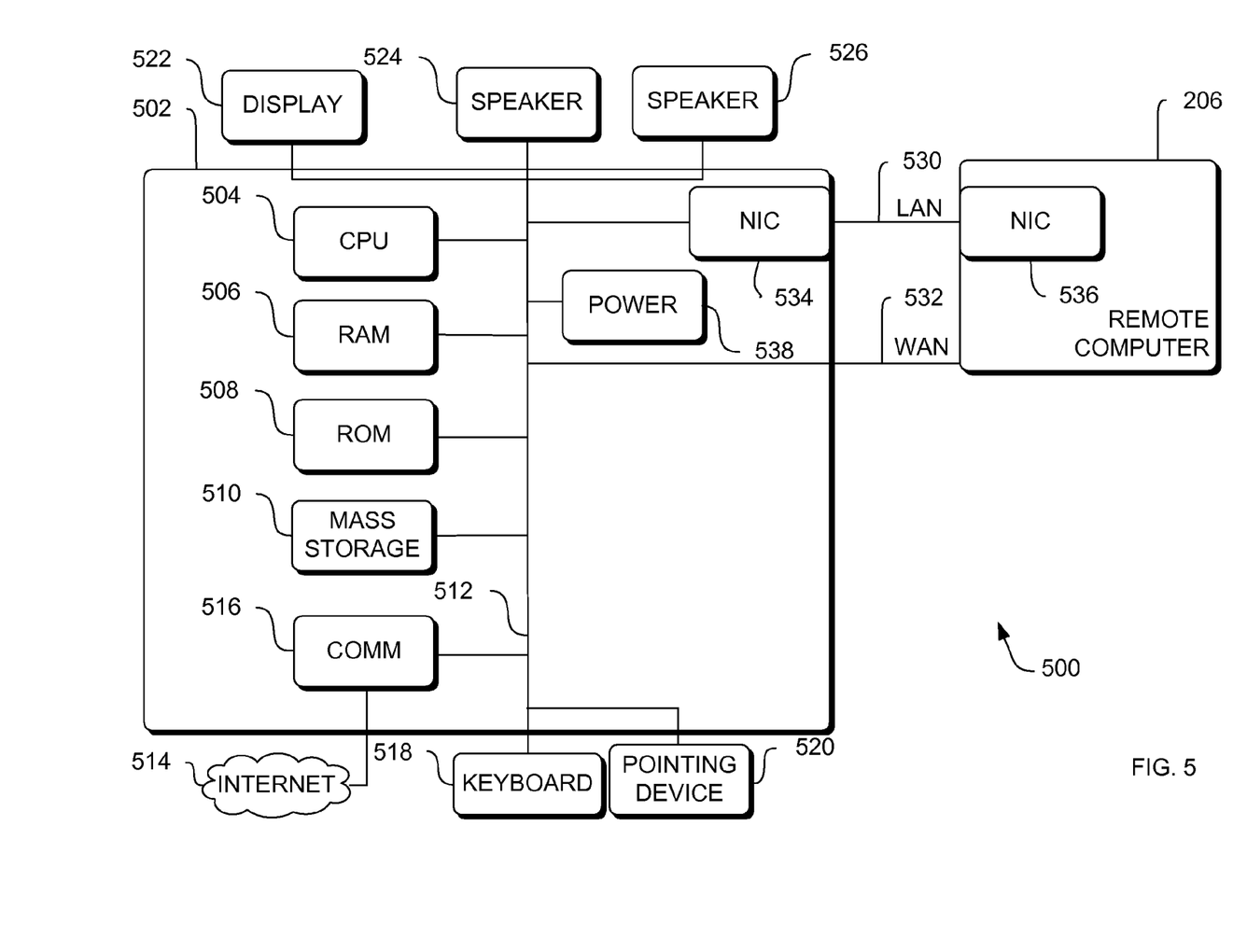
FIG. 5 is a block diagram of the hardware and operating environment in which different embodiments can be practiced.

In some embodiments, method 600 is implemented as a computer data signal embodied in a carrier wave, that represents a sequence of instructions which, when executed by a processor, such as processor 504 in FIG. 5, cause the processor to perform the respective method. In other embodiments, method 600 is implemented as a computer-accessible medium having executable instructions capable of directing a processor, such as processor 504 in FIG. 5, to perform the respective method. In varying embodiments, the medium is a magnetic medium, an electronic medium, or an optical medium.

Hardware and Operating Environment

FIG. 5 is a block diagram of the hardware and operating environment 500 in which different embodiments can be practiced. The description of FIG. 5 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 502 includes a processor 504, commercially available from Intel, Motorola, Cyrix and others. Computer 502 also includes random-access memory (RAM) 506, read-only memory (ROM) 508, and one or more mass storage devices 510, and a system bus 512, that operatively couples various system components to the processing unit 504. The memory 506, 508, and mass storage devices, 510, are types of computer-accessible media. Mass storage devices 510 are more specifically types of nonvolatile computer-accessible media and can include one or more hard disk drives, floppy disk drives, optical disk drives, and tape cartridge drives. The processor 504 executes computer programs stored on the computer-accessible media.

Computer 502 can be communicatively connected to the Internet 514 via a communication device 516. Internet 514 connectivity is well known within the art. In one embodiment, a communication device 516 is a modem that responds to communication drivers to connect to the Internet via what is known in the art as a "dial-up connection." In another embodiment, a communication device 516 is an Ethernet® or similar hardware network card connected to a local-area network (LAN) that itself is connected to the Internet via what is known in the art as a "direct connection" (e.g., T1 line, etc.).

A user enters commands and information into the computer 502 through input devices such as a keyboard 518 or a pointing device 520. The keyboard 518 permits entry of textual information into computer 502, as known within the art, and embodiments are not limited to any particular type of keyboard. Pointing device 520 permits the control of the screen pointer provided by a graphical user interface (GUI) of operating systems such as versions of Microsoft Windows®. Embodiments are not limited to any particular pointing device 520. Such pointing devices include mice, touch pads, trackballs, remote controls and point sticks. Other input devices (not shown) can include a microphone, joystick, game pad, satellite dish, scanner, or the like.

In some embodiments, computer 502 is operatively coupled to a display device 522. Display device 522 is connected to the system bus 512. Display device 522 permits the display of information, including computer, video and other information, for viewing by a user of the computer. Embodiments are not limited to any particular display device 522. Such display devices include cathode ray tube (CRT) displays (monitors), as well as flat panel displays such as liquid crystal displays (LCD's). In addition to a monitor, computers typically include other peripheral input/output devices such as printers (not shown). Speakers 524 and 526 provide audio output of signals. Speakers 524 and 526 are also connected to the system bus 512.

Computer 502 also includes an operating system (not shown) that is stored on the computer-accessible media RAM 506, ROM 508, and mass storage device 510, and is and executed by the processor 504. Examples of operating systems include Microsoft Windows®, Apple MacOS®, Linux®, UNIX®. Examples are not limited to any particular operating system, however, and the construction and use of such operating systems are well known within the art.

Embodiments of computer 502 are not limited to any type of computer 502. In varying embodiments, computer 502 comprises a PC-compatible computer, a MacOS®-compatible computer, a Linux®-compatible computer, or a UNIX®-compatible computer. The construction and operation of such computers are well known within the art.

Computer 502 can be operated using at least one operating system to provide a graphical user interface (GUI) including a user-controllable pointer. Computer 502 can have at least one web browser application program executing within at least one operating system, to permit users of computer 502 to access intranet or Internet world-wide-web pages as addressed by Universal Resource Locator (URL) addresses. Examples of browser application programs include Netscape Navigator® and Microsoft Internet Explorer®.

The computer 502 can operate in a networked environment using logical connections to one or more remote computers, such as remote computer 528. These logical connections are achieved by a communication device coupled to, or a part of, the computer 502. Embodiments are not limited to a particular type of communications device. The remote computer 528 can be another computer, a server, a router, a network PC, a client, a peer device or other common network node. The logical connections depicted in FIG. 5 include a local-area network (LAN) 530 and a wide-area network (WAN) 532. Such networking environments are commonplace in offices, enterprise-wide computer networks, intranets and the Internet.

When used in a LAN-networking environment, the computer 502 and remote computer 528 are connected to the local network 530 through network interfaces or adapters 534, which is one type of communications device 516. Remote computer 528 also includes a network device 536. When used in a conventional WAN-networking environment, the computer 502 and remote computer 528 communicate with a WAN 532 through modems (not shown). The modem, which can be internal or external, is connected to the system bus 512. In a networked environment, program modules depicted relative to the computer 502, or portions thereof, can be stored in the remote computer 528.

Computer 502 also includes power supply 538. Each power supply can be a battery.

CONCLUSION

A method and apparatus for exposure optimization has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in object-oriented terms, one of ordinary skill in the art will appreciate that implementations can be made in a procedural design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The system components can be embodied as computer hardware circuitry or as a computer-readable program, or a combination of both. In another embodiment, system components can be implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 502 in FIG. 5, or on at least as many computers as there are components.

I claim:

1. An imaging system having an imaging source and an imaging detector for forming an image upon detection of a signal from the imaging source, the imaging system comprising:
   an interface capable of receiving exposure characteristic data wherein the exposure characteristic data includes at least one region of interest for at least one subsequent diagnostic image, wherein each of the at least one region of interest is segmented from a mixture of spatial and statistical processes in which collimator and raw radiation areas are removed from the diagnostic image using morphological operations and the anatomical contents of the diagnostic image are delineated using a gradient filter that identifies boundaries;
   a controller for determining a plurality of control parameters based on the received exposure characteristic data; and
   a device placed between the imaging source and the imaging detector for generating a control signal upon the occurrence of the plurality of control parameters.

2. The imaging system of claim 1, wherein the interface further comprises:
   an interface operable to support communication based on at least one of infrared, low power RF, ultrasonic serial communications, optical communication, or dedicated line.

3. The imaging system of claim 1, wherein the exposure characteristic data further comprises:
   at least one of system level performance limitation, exposure information, exposure start, or calibration information.

4. The imaging system of claim 1, wherein the plurality of control parameters further comprises:
   spectrum compensation, timing compensation, exposure start, exposure termination, and imaging related information.

5. The imaging system of claim 4, further comprising:
   a calibration module operable to independently calibrating the device placed between the imaging source and the imaging detector.

6. The imaging system of claim 5, wherein the exposure termination further comprises:
   a single bit and requires a timing resolution of approximately 0.1 mS.

7. An apparatus in an X-ray system, the X-ray system comprising a source of X-rays and a detector to generate detection data in response to the X-rays, the apparatus operable to generate an X-ray image while controlling a dose of X-rays received in order to generate the image, the apparatus operable to generate an X-ray image comprising:
   a receiving interface capable of receiving exposure characteristic data, wherein the exposure characteristic data includes at least one region of interest for generated detection data, wherein each of the at least one region of interest is segmented from a mixture of spatial and statistical processes in which collimator and raw radiation areas are removed from the generated detection data using morphological operations and the anatomical contents of the diagnostic image are delineated using a gradient filter that identifies boundaries;
   an exposure module for extracting data of interest from the generated detection data;
   an analog to digital conversion module for converting the extracted data of interest having signal-to-noise ratios that correspond to an X-ray dosage level; and
   a generating interface placed between the source of X-rays and the detector for generating exposure control data,
   wherein the X-ray system selects the dose of X-rays received at the detector based on the generated exposure control data.

8. The apparatus of claim 7, wherein the analog to digital conversion module further comprises:
   an analog to digital conversion module operable to:
   generate the signal-to-noise ratios from a required signal-to-noise ratios and a measured signal-to-noise ratios,
   generate the measured signal-to-noise ratios in response to the data of interest,
   generate the required signal-to-noise ratios from a predetermined selected anatomy/view, wherein the predetermined selected anatomy/view further comprises a pre-determined selected anatomy/view stored in the exposure module.

9. The apparatus of claim 8 further comprising:
an apparatus operable to control the X-ray dosage level by adjusting an exposure time or by adjusting a current of the source of X-rays and an exposure time.

10. The apparatus of claim 7 further comprising:
an apparatus operable to:
determine a voltage level for a selected anatomy/view of the source of X-rays; and
apply the voltage level to the source of X-rays.

11. The apparatus of claim 10, wherein the apparatus operable to generate the exposure control data further comprises:
apparatus operable to transmit the generated exposure control data through at least one of infrared, low power –RF, ultrasonic serial communications, optical communication, or dedicated line, and wherein the apparatus operable to receive further comprises:
apparatus operable to receive the exposure characteristic data through at least one of infrared, low power –RF, ultrasonic serial communications, optical communication, or dedicated line.

12. The apparatus of claim 11, wherein the exposure characteristic data further comprises:
at least one of region of interest for at least one subsequent diagnostic image, at least one of system level performance limitation, exposure information, exposure start, or calibration information.

13. The apparatus of claim 12, wherein the plurality of control parameters further comprises:
spectrum compensation, timing compensation, exposure start, exposure termination, and imaging related information.

14. A method for controlling a dose of X-rays received in order to generate an X-ray image, the method performed by an X-ray imaging system, the X-ray imaging system having signal source, signal detector, and an apparatus placed between the signal source and the signal detector for generating an X-ray image, the method further comprising:
receiving exposure characteristic data from the X-ray imaging system, wherein the exposure characteristic data includes at least one region of interest for at least one X-ray image, wherein each of the at least one region of interest is segmented from a mixture of spatial and statistical processes in which collimator and raw radiation areas are removed from the X-ray image using morphological operations and the anatomical contents of the diagnostic image are delineated using a gradient filter that identifies boundaries;
extracting data of interest from the generated detection data;
converting the extracted data of interest so as to produce a signals having signal-to-noise ratios that correlate to an X-ray dosage level; and
generating exposure control data to the X-ray system for controlling the dosage of X-rays received at the detector.

15. The method of claim 14, wherein the method further comprises:
generating a measured signal-to-noise ratio in response to the data of interest;
generating a required signal-to-noise ratio from a pre-determined selected anatomy/view; the pre-determined selected anatomy/view being stored in an exposure module; and
generating the signal-to-noise ratios from the required signal-to-noise ratio and the measured signal-to-noise ratio.

16. The method of claim 15 further comprising:
controlling the X-ray dosage by adjusting an exposure time or by adjusting a current of the source of X-rays and an exposure time.

17. The method of claim 14 further comprising:
determining a voltage level for a selected anatomy/view of the source of X-rays; and
applying the voltage level to the source of X-rays.

18. The method of claim 17, wherein the generating of the exposure control data further comprises:
transmitting the generated exposure control data through at least one of infrared, low power –RF, ultrasonic serial communications, optical communication, or dedicated line, and
the receiving further comprises:
receiving the exposure characteristic data through at least one of infrared, low power –RF, ultrasonic serial communications, optical communication, or dedicated line.

19. The method of claim 18, wherein the exposure characteristic data further comprises:
at least one of region of interest for at least one subsequent diagnostic image, at least one of system level performance limitation, exposure information, exposure start, or calibration information.

20. The method of claim 19, wherein the plurality of control parameters further comprise:
spectrum compensation, timing compensation, exposure start, exposure termination, and imaging related information.

* * * * *